United States Patent [19]

Chucholowski et al.

[11] Patent Number: 5,073,565

[45] Date of Patent: Dec. 17, 1991

[54] TETRAZOLE UREAS AND THIOUREAS AND THEIR USE AS ACAT INHIBITORS

[75] Inventors: Alexander W. Chucholowski, Bad Krozingen, Fed. Rep. of Germany; Andrew D. White, Lakeland, Mich.

[73] Assignee: Warner-Lambert Company, Morris Plain, N.J.

[21] Appl. No.: 515,984

[22] Filed: Apr. 27, 1990

[51] Int. Cl.$^5$ .................... C07D 257/06; A61K 31/41
[52] U.S. Cl. ...................................... 514/381; 548/251
[58] Field of Search ........................ 548/251; 514/381

[56] References Cited
PUBLICATIONS

Chem. Abst. 76:25184v (1972).
J. Med. Chem. 22:28–32 (1979).
Berge, et al., J. Pharm. Sciences, 66:1–19 (1977).
Field, et al., Biochem. et Biophys., 712:557–570 (1982).

Primary Examiner—David B. Springer
Attorney, Agent, or Firm—Ruth H. Newtson

[57] ABSTRACT

Novel ACAT inhibitors useful in the treatment of atherosclerosis which are N-aryl-N'-tetrazole ureas and thioureas.

20 Claims, No Drawings

TETRAZOLE UREAS AND THIOUREAS AND THEIR USE AS ACAT INHIBITORS

BACKGROUND OF THE INVENTION

This invention relates to chemical compounds having pharmacological activity, to pharmaceutical compositions which include these compounds, and to a pharmaceutical method of treatment. More particularly, this invention concerns certain novel compounds which inhibit the enzyme acylcoenzyme A: cholesterol acyltransferase (ACAT), pharmaceutical compositions containing these compounds, and a method of treating hypercholesterolemia and atherosclerosis.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which could be effective in lowering total serum cholesterol levels. It is now known that cholesterol is transported in the blood in the form of complex particles consisting of a core of cholesteryl esters plus triglycerides and an exterior consisting primarily of phospholipids and a variety of types of protein which are recognized by specific receptors. For example, cholesterol is carried to the sites of deposit in blood vessels in the form of low density lipoprotein cholesterol (LDL cholesterol) and away from such sites of deposit by high density lipoprotein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme acyl-CoA: cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

INFORMATION DISCLOSURE STATEMENT

Chemical Abstracts 76:25184v (1972) reports the synthesis of N-phenyl-N'-(1-phenyl-1H-tetrazol-5-yl)-urea. No utility for the compound is given.

J. Medicinal Chemistry 22,28-32 (1979) reports anti-leukemic data for N-(4-ethoxycarbonylphenyl)-N'-tetrazol-5-yl-urea showing the compound to be inactive.

SUMMARY OF INVENTION

The present invention provides a class of compounds which have acyl-CoA:cholesterol acyltransferase transferase (ACAT) inhibitory activity and intermediates useful in preparing said compounds having the following structure:

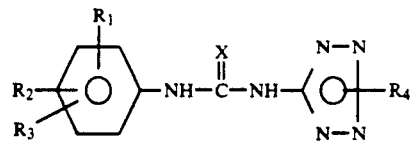

Formula I wherein X is oxygen or sulfur; wherein each of $R^1$, $R^2$, and $R^3$ is the same or different and is selected from
hydrogen,
fluorine,
chlorine,
bromine,
a straight or branched alkyl group having from one to six carbon atoms,
a straight or branched alkoxy group having from one to six carbon atoms,
benzoyl which is unsubstituted or is substituted on the aromatic ring with from one to three substituents selected from fluorine, chlorine, bromine, iodine, a straight or branched alkyl group having from one to six carbon atoms or a straight or branched alkoxy group having from one to six carbon atoms,
benzyl which is unsubstituted or is substituted on the aromatic ring with from one to three substituents selected from fluorine, chlorine, bromine, iodine, a straight or branched alkyl group having from one to six carbon atoms or a straight or branched alkoxy group having from one to six carbon atoms,
phenyl which is unsubstituted or is substituted with from one to three substituents selected from fluorine, chlorine, bromine, iodine, a straight or branched alkyl group having from one to six carbon atoms, or a straight or branched alkoxy group having from one to six carbon atoms;
—$NR_5R_6$ wherein each of $R_5$ and $R_6$ is the same or different and is hydrogen, a straight or branched alkyl group having from one to four carbon atoms or —$NR_5R_6$ taken together form a monocyclic heterocyclic group selected from pyrrolidino, piperidino, piperazino or piperazino substituted on the 4-position with a straight or branched alkyl group having from one to four carbon atoms;
—$COR_7$ wherein $R_7$ is hydroxy, a straight or branched alkoxy group having from one to six carbon atoms, benzyloxy which is unsubstituted or is substituted on the aromatic ring with from one to three substituents selected from fluorine, chlorine, bromine, iodine, a straight or branched alkyl group having from one to six carbon atoms, or a straight or branched alkoxy group having from one to six carbon atoms, or $R_7$ is —$NR_5R_6$ wherein $R_5$ and $R_6$ have the meanings defined above;

wherein $R_4$ is attached to either the 1- or 2-position of the tetrazole ring and is selected from
(a) a straight or branched hydrocarbon chain having from 1 to 20 carbon atoms and which is saturated or contains from one to three double bonds and wherein said chain is unsubstituted or is substituted with one or two substituents selected from fluorine, chlorine, bromine, iodine, straight or branched alkoxy having from on to four carbon atoms, hydroxy or tetrahydropyran-6-yloxy;
(b) a spiroalkyl group of the formula

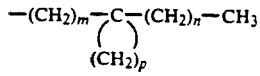

wherein each of m and n is independently zero or one to six, and p is two to six;

(c) the group —(CH$_2$)$_q$NR$_8$R$_9$ wherein q is two to four and each of R$_8$ an R$_9$ is hydrogen or a straight or branched alkyl group having from 1 to 20 carbon atoms, provided that one of R$_8$ and R$_9$ is other than hydrogen; or (d) the group —(CH$_2$)$_r$-phenyl wherein r is zero to four and the phenyl moiety is unsubstituted or is substituted with from one to three substituents selected from fluorine, chlorine, bromine, iodine, a straight or branched alkyl group having from one to six carbon atoms, or a straight or branched alkoxy group having from one to six carbon atoms; and pharmaceutically acceptable salts thereof with the proviso that when R$_4$ is phenyl on the 1-position of the tetrazole ring at least one of R$_1$, R$_2$, and R$_3$ is other than hydrogen.

DETAILED DESCRIPTION OF THE INVENTION

The present invention provides a novel class of compounds which contain a tetrazole moiety and which are ACAT inhibitors rendering them useful in treating hypercholesterolemia and atherosclerosis. The compounds of Formula I wherein R$_4$ is a straight or branched hydrocarbon chain having from 1 to 20 carbon atoms and is substituted with tetrahydropyran-6-yloxy are also useful as intermediates to prepare compounds of Formula I, as will become apparent by the specific examples.

Illustrative examples of straight or branched saturated hydrocarbon chains having from 1 to 20 carbon atoms, which the group R$_4$ may represent, include methyl, ethyl, n-propyl, isopropyl, n-butyl, iso-butyl, tert-butyl, n-pentyl, isopentyl, n-hexyl, n-heptyl, n-octyl, n-undecyl, n-dodecyl, n-hexadecyl, 2,2-dimethyldodecyl, 2-ethyltetradecyl, and n-octadecyl groups.

Illustrative examples of straight or branched hydrocarbon chains having from 1 to 20 carbon atoms and having from 1 to 3 double bonds which the group R$_4$ may represent include ethenyl, 2-propenyl, 2-butenyl, 3-pentenyl, 2-octenyl, 5-nonenyl, 4-undecenyl, 5-heptadecenyl, 3-octadecenyl, 9-octadecenyl, 2,2-dimethyl-11-eicosenyl, 9,12-octadecadienyl, and hexadecenyl.

Straight or branched alkoxy groups having from one to four carbon atoms as used herein include, for example, methoxy, ethoxy, n-propoxy, t-butoxy, or having from one to six carbon atoms include for example additionally n-pentoxy, 3-ethylpropoxy, 5-methylpentoxy, and n-hexyloxy.

Illustrative example of straight or branched alkyl groups having from one to four carbon atoms as used herein include methyl, ethyl, n-propyl, isopropyl, n-butyl, tert-butyl or having from one to six carbon atoms include additionally n-pentyl, 2-methylbutyl, 4-methylpentyl, n-hexyl, and 5-methyl-pentyl.

Preferred compounds of this invention are those of general Formula I wherein X is oxygen and more preferred are those wherein R$_4$ is on the 2-position of the tetrazole ring. Also, more preferred compounds are those wherein R$_1$, R$_2$, R$_3$, R$_5$, and R$_6$ are independently selected from straight or branched alkyl having from one to six carbon atoms. Preferred compounds of this invention may be depicted by the following Formula II:

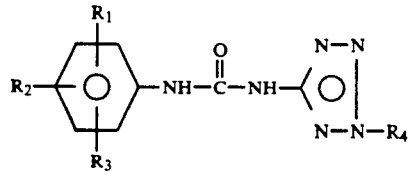

Formula II wherein R$_1$, R$_2$, R$_3$, and R$_4$ have the meanings defined in Formula I. Compounds of Formula II wherein R$_4$ is a straight or branched hydrocarbon chain having from 11 to 15 carbon atoms which is saturated or contains from one to three unsaturations are more preferred, and compounds of Formula II wherein R$_1$, R$_2$, and R$_3$ are straight or branched alkyl having from one to six carbon atoms, straight or branched alkoxy having from one to six carbon atoms or fluoro are more preferred. Also compounds of Formula II wherein R$_4$ is —(CH$_2$)$_r$-phenyl wherein r is one or two are preferred. In the most preferred compounds of Formula II R: is hydrogen and each of R$_2$ and R$_3$ is isopropyl substituted in the 2,6-positions or each of R$_1$, R$_2$, and R$_3$ is methoxy substituted in the 2,4,6-positions, or each of R$_1$, R$_2$, and R$_3$ is fluoro substituted in the 2,4,6-positions.

Pharmaceutically acceptable salts of the compounds of Formulas I and II are also included in the scope of the present invention.

The acid salts may be generated from the free base by reaction of the latter with one equivalent of a suitable nontoxic, pharmaceutically acceptable acid, followed by evaporation of the solvent employed for the reaction and recrystallization of the salt if required. The free base may be recovered from the acid salt by reaction of the salt with an aqueous solution of a suitable base such as sodium carbonate, sodium bicarbonate, potassium carbonate, sodium hydroxide, and the like.

Suitable acids for forming acid salts of the compounds of this invention include, but are not necessarily limited to acetic, benzoic, benzene-sulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The class of acids suitable for the formation of nontoxic, pharmaceutically acceptable salts is well known to practitioners of the pharmaceutical formulation arts (see, for example, Stephen N. Berge, et al, *J Pharm*Sciences, 66:1-19 (1977)).

The compounds of the present invention may also exist in different stereoisomeric forms by virtue of the presence of asymmetric centers in the compound. The present invention contemplates all stereoisomeric forms of the compounds as well as mixtures thereof, including racemic mixtures.

Further, the compounds of this invention may exist in unsolvated as well as solvated forms with pharmaceutically acceptable solvents such as water, ethanol and the like. In general, the solvated forms are considered equivalent to the unsolvated forms for the purposes of this invention.

As shown by the data presented below in Table 1, the compounds of the present invention are potent inhibitors of the enzyme acyl-CoA: cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described in Field, F. J. and Salone, R. G., *Biochemica et Biophysica*, 712:557–570 (1982). The test assesses the ability of a test compound to inhibit the acylation of cholesterol by oleic acid by measuring the amount of radiolabeled cholesterol oleate formed from radiolabeled oleic acid in a tissue preparation containing rabbit intestinal microsomes.

The data appear in Table I where they are expressed in $IC_{50}$ values; i.e., the concentration of test compound required to inhibit the activity of the enzyme by 50%.

TABLE I

| Compound of Example | $IC_{50}$ ($\mu M$) |
|---|---|
| 1 (c) | 0.036 |
| 1 (d) | 0.021 |
| 3 | 0.012 |
| 4 | 0.009 |
| 5 | 0.014 |
| 6 | 0.057 |
| 7 | 0.012 |
| 10 | 0.009 |
| 11 | 0.092 |
| 15 | 0.072 |
| 17 | 0.37 |
| 19 | 0.30 |
| 20 | 0.18 |
| 21 | 0.327 |
| 22 | 0.059 |
| 23 | 0.073 |
| 24 | 0.014 |

In one in vivo screen designated APCC, male Sprague-Dawley rats (200 to 225 g) were randomly divided into treatment groups and dosed at 4 PM with either vehicle (CMC/Tween) or suspensions of compounds in vehicle. The normal chow diet was then replaced with the PCC diet (5.5% peanut oil, 1.5% cholesterol, and 0.5% cholic acid). The rats consumed this diet a libitum during the night and were sacrificed at 8 AM to obtain blood samples for cholesterol analysis using standard procedures. Statistical differences between mean cholesterol values for the same vehicle were determined using analysis of variance followed by Fisher's least significant test. The results of this trail for representative compounds of the present invention appear in Table II wherein percent change means the difference in total cholesterol between control, and the drug-treated animals, and the (mg/dL) is the milligrams of compound per deciliter of vehicle administered. The milligrams are reflected parenthetically.

TABLE II

| Compound of Example | % Change (mg/dl) |
|---|---|
| 1 (c) | −42 (30) |
| 1 (d) | −54 (30) |
| 3 | −55 (30) |
| 4 | −50 (30) |
| 5 | −54 (30) |
| 6 | −58 (30) |
| 7 | −56 (30) |
| 10 | −45 (30) |
| 17 | N/C (50) |
| 19 | −26 (50) |
| 20 | −47 (50) |
| 22 | −50 (30) |
| 23 | −28 (30) |
| 24 | −50 (30) |

N/C means no change.

In therapeutic use as agents for treating hypercholesterolemia or atherosclerosis, the compounds of Formula I or pharmaceutically acceptable salts thereof are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing the pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

Powders and tablets preferably contain between about 5% to about 70% by weight of the active ingredient. Suitable carriers are magnesium dicarbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner cachets are also included. Tablets, powders, cachets, and capsules can be used as solid dosage forms suitable for oral administration.

Liquid form preparations include solutions, suspensions, or emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethylcellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation containing discrete quantities of the preparation, for example, packeted tablets, capsules, and powders in vials or ampoules. The unit dosage form can also be a capsule, cachet, or tablet itself, or it can be the appropriate number of these packaged forms.

The compounds of this invention are prepared by procedures generally known in the art. For example, the compounds of this invention may be prepared as generally set forth in Charts I and II wherein the various symbols $R_1$, $R_2$, $R_3$, $R_4$, and X have the meanings defined in Formula I. Preferably the compounds of Formula I wherein $R_4$ is on the 2-position of the tetrazole ring are prepared as set forth in Chart I, and the compounds of Formula I wherein $R_4$ is one the 1-position of the tetrazole ring are prepared as set forth in Chart II. Referring to Chart I, the isocyanate or thioisocyanate (1) and the tetrazoleamine (2) are refluxed overnight or for about 12 hours in acetonitrile to give the unsubstituted tetrazole urea compounds (3) which are treated with an appropriate alkylating agent (4) in acetonitrile, heating to reflux in the presence of a tertiary amine such as triethylamine. The alkylation reaction yields predominantly the two-substituted tetrazole compounds (6) with the one-substituted tetrazole (5) being isolated as the minor product of the reaction.

In Chart II there is set forth an alternative method for the preparation of the compounds of the present invention whereby the tetrazole-amine (1) is treated with an appropriate alkylating agent (2) using equimolar amounts of each in an aqueous lower alcohol, such as ethanol, in the presence of a base such as sodium or potassium hydroxide. The alkylation is carried out at reflux for 12 to 20 hours. The resulting substituted tetrazole-amine (3) and (4) is then reacted with an appropriate isocyanate or thioisocyanate in acetonitrile in the presence of a tertiary amine such as triethylamine by heating at reflux for about 12 hours to give the final products (5) and (6).

The alkylating agents $R_4Br$ are commercially available or are prepared by procedures generally known in the art. To prepare akylating agents of the formula $Br(CH_2)_qNR_8R_9$ wherein q, $R_8$, and $R_9$ have the meanings define in Formula I two procedures may be used. For alkylating agents wherein q is three or four a suitable protected bromoalcohol of the formula ⓟO(CH$_2$)$_x$Br wherein x is three or four and ⓟ is a suitable protecting group is reacted with an amine of formula $R_8R_9NH$ wherein $R_8$ and $R_9$ have the meanings defined in Formula I to give the protected alcohol amine ⓟO(CH$_2$)$_x$—NR$_8$R$_9$ which is converted to the aminoalkyl bromide by standard techniques. Suitable protecting groups are those well known in the art and include, for example, tetrahydropyran and silyl protecting groups such as t-butyl dimethylsilyl. For alkylating agents wherein q is two an amine of the formula $HNR_8R_9$ is reacted with an epoxide to give $HOCH_2CH_2NR_8R_9$ which is converted to the aminoalkylbromide by standard procedures.

The following specific examples further illustrate the invention.

EXAMPLE 1

N-[2,6-Bis(1-methylethyl)phenyl]-N'-[2-(12-hydroxydodecyl)-2H-tetrazol-5-yl] urea (a) 2-(12-Bromododecyloxy)tetrahydropyran 12-Bromo-dodecan-1-ol (5.12 g, 19.3 mmol) was added to a vigorously stirred solution of dihydropyran (2.1 mL, 23.2 mmol) and Amberlyst H15 (0.25 g, Aldrich D10,620-8) in hexane (100 mL). After 3 hours dihydropyran (2.1 mL) was added and the solution stirred for a further 15 hours. The mixture was then filtered, and the filtrate concentrated in vacuo and chromatographed graphed on silica gel, eluting with 2% ethyl acetate in hexane to give the title compound, (a), 8.02 g (75%), as an oil.

(b) N-[2,6-Bis(1-methylethyl)phenyl]-N'-(1H-tetrazol-5-yl)urea

5-Aminotetrazole hydrate (45 g, 0.44 mol) was refluxed in toluene (300 mL) in the presence of a Dean-Stark trap. After removal of the theoretical amount of water (7.9 mL) the mixture was allowed to cool, concentrated in vacuo, and the resulting solid stirred with acetonitrile (500 mL). Triethylamine (61 mL, 0.44 mol) and 2,6-diisopropyl phenylisocyanate (89.3 mL, 0.44 mol) were added sequentially and the mixture refluxed for 4 hours. The mixture was then allowed to cool, concentrated in vacuo to about 200 mL, and acidified with 1M citric acid. The solid was filtered, washed with water (1L), ethyl acetate (1L), and dried in vacuo to give the title compound (b), m.p. >240° C.

Expected %: C, 58.32; H, 6.99; N, 29.14;
Found %: C, 58.23; H, 7.01, N, 29.23.

(c) N-[2,6-Bis(1-methylethyl)phenyl]-N'-2-[[tetrahydro-2H-pyran-2-yl) oxy]dodecyl]-2H-tetrazol-5-yl]urea 1-Bromo-12-(tetrahydro-2H-pyran-2-yl)oxydodecane (8.0 g, 0.023 mol) was added to a refluxing mixture of N-[2,6-bis(1-methylethyl)phenyl]-N'-(1H-tetrazol5-yl)-urea (6.6 g, 0.023 mol), triethylamine (2.54 g, 0.025 mol) and acetonitrile (200 mL). The mixture was allowed to reflux for 18 hours, allowed to cool, and concentrated to one-third volume. The slurry obtained was filtered and the filtrate concentrated in vacuo and columned on silica gel, eluting with 15% to 20% ethyl acetate in hexanes to give a white solid (4.46 g, 35%), m.p. 110–113° C.

(d) The product from (c) above (3.8 g, 6.8 mmol) was stirred at room temperature with p-toluene sulphonic acid (50 mg) in methanol (200 mL) for 1.5 hours. The solution was then concentrated in vacuo and taken up in ethyl acetate (20 mL). Hexane (200 mL) was added and the resultant precipitate filtered to give N-[2,6-bis(1-methylethyl)phenyl]-N'-[2-(12-hydroxy-dodecyl)-2H-tetrazol-5-yl]urea, a white solid, 2.89 g, ( m.p. 80–90° C.

EXAMPLE 2

N-[2,6-Bis(1-methylethyl)phenyl]-N'-[1-dodecyl-1H-tetrazol-5-yl]urea (a) 5-Amino-1-dodecyltetrazole and 5-Amino-2-dodecyl-tetrazole 1-Bromododecane (46.8 g, 0.188 mol) was added in one portion to a refluxing solution of hydrated 5-aminotetrazole (20.0 g, 0.19 mol) and sodium hydroxide (8 g, 0.2 mol) in 550 mL of ethanol/water (4:1.5 by volume). The resulting mixture was refluxed for 18 hours, allowed to cool, filtered, washed with ethanol (2 ×50 mL), and the resulting solid dried in vacuo to give 17.85 g of a mixture of isomers. The mixture was recrystallized from acetonitrile (250 mL) to give 6.85 g of 5-amino-1-dodecyltetrazole.

To obtain 5-amino-2-dodecyltetrazole the crude reaction filtrate from above was concentrated to two-thirds volume in vacuo and allowed to crystallize. The mixture was filtered to yield a solid, which was dried in vacuo to give 9.95 g of 5-amino-2-dodecyltetrazole.

(b) Triethylamine (2.50 mL, 18.0 mmol) was added to a slurry of 5-amino-1-dodecyltetrazole (4.56 g, 18.0 mmol) in acetonitrile (150 mL). The mixture was heated to reflux and upon dissolution of the solid, 2,6-diisopropylphenyl isocyanate (3.90 mL, 18.1 mmol) was added in one portion. The solution was refluxed for 18 hours and allowed to cool. The resultant precipitate was filtered and the filtrate concentrated in vacuo and partitioned between ethyl acetate and water (1:1). The organic layer was washed with brine, dried over $Na_2SO_4$, filtered, concentrated in vacuo, and columned on silica gel, eluting with 10% then 15% ethyl acetate in hexanes to give an oil which solidified on standing to give the title compound as a white solid (1.95 g, 24%), m.p. 80–88° C.

EXAMPLE 3

N-[2,6-bis(1-methylethyl)phenyl]-N'-(2-tetradecyl-2H-tetrazol-5-yl)urea

1-Bromotetradecane (26.1 g, 0.094 mol) was added to a refluxing solution of N-[2,6-bis(1-methylethyl)-phenyl]-N'-(1H'-tetrazol-5-yl)urea (24.8 g, 0.086 mol), triethylamine (9.51 g, 0.094 mol) and acetonitrile (300 mL). The mixture was allowed to reflux for 18 hours, cooled, filtered, and the solid obtained recrystallized from hot acetonitrile to give a white solid (25.0 g, 60%), m.p. 112–114° C.

EXAMPLE 4

N-[2,6-Bis(1-methylethyl)phenyl]-N'-(2-tridecyl-2H-tetrazol-5-yl)urea

1-Bromotridecane (5.48 g, 0.022 mol) was added to a refluxing solution of N-[2,6-bis(1-methylethyl)-phenyl]-N'-(1H'-tetrazol-5-yl)urea (6.0 g, 0.021 mol), triethylamine (2.1 g, 0.021 mol) and acetonitrile (175 mL). The solution was refluxed for 6 days and cooled, concentrated and partitioned between 1M citric acid and ethyl acetate. The organics were washed with water, dried $Na_2SO_4$, concentrated in vacuo and columned on silica gel eluting with 15% ethyl acetate in hexane (preload compound in acetonitrile/ethyl acetate 1:1) to give a white solid (1.2 g, 12%), m.p 110–114° C.

When in the procedure of Example 3 an appropriate amount of the bromide listed in the following Table A was substituted for 1-bromotetradecane and the general procedure of Example 3 is followed, the compounds listed in Table A were obtained.

TABLE A

| Bromide | Compound | Example Number |
| --- | --- | --- |
| 1-Bromododecane | N-[2,6-Bis(1-methylethyl)-phenyl]-N'-(2-dodecyl-2H-tetrazol-5-yl)urea, m.p. 117–119° C. | 5 |
| 1-Bromohexadecane | N-[2,6-Bis(1-methylethyl)-phenyl]-N'-(2-hexadecyl-2H-tetrazol-5-yl)urea, m.p. 108–111° C. | 6 |
| 2-(10-Bromodecyloxy)tetrahydropyran | N-[2,6-Bis(1-methylethyl)-phenyl]-N'-[2-[(tetrahydro-2H-pyran-2-yl)oxy]decyl-2H-tetrazol-5-yl]-urea, m.p. 110–115° C. | 7 |
| 1-Bromononane | N-[2,6-Bis(1-methylethyl)-phenyl]-N'-(2-nonyl-2H-tetrazol-5-yl)urea, m.p. 128–130° C. | 8 |
| 2-(11-Bromoundecyloxy)tetrahydropyran | N-[2,6-Bis(1-methylethyl)-phenyl]-N'-[2-[(tetrahydro-2H-pyran-2-yl)oxy]undecyl-2H-tetrazol-5-yl]urea, | 9 |

TABLE A-continued

| Bromide | Compound | Example Number |
| --- | --- | --- |
| | m.p. 105–111° C. | |

When in the procedure of Example 4 an appropriate amount of the bromide listed below in Table B is substituted for 1-bromotridecane and the general procedure of Example 4 is followed the compounds listed in Table B were obtained.

TABLE B

| Bromide | Compound | Example Number |
| --- | --- | --- |
| 1-Bromoundecane | N-[2,6-Bis(1-methylethyl)-phenyl]-N'-(2-undecyl-2H-tetrazol-5-yl)urea, m.p. 119–121° C. | 10 |
| 1-Bromobutane | N-[2,6-Bis(1-methylethyl)-phenyl]-N'-(2-butyl-2H-tetrazol-5-yl)urea, m.p. 174–179° C. | 11 |
| Geranylbromide | N-[2,6-Bis(1-methylethyl)-phenyl]-N'-[2-(3,7-dimethyl-2,6-octadienyl)-2H-tetrazol-5-yl]urea, m.p. 98–107° C. | 12 |
| 11-Bromoundecanoic acid methyl ester | N-[2,6-Bis(1-methylethyl)-phenyl]-N'-[2-(10-methoxycarbonyldecyl)-2H-tetrazol-5-yl]urea, m.p. 80–85° C. | 13 |

When in the procedure of Example 1(d) an appropriate amount of N-[2,6-bis(1-methylethyl)-phenyl]-N'-[2-[(tetrahydro-2H-pyran-2-yl)oxy]undecyl]-2H-tetrazol-5yl]urea or N-[2,6-bis(1-methylethyl)-phenyl]-N'-[2- [(tetrahydro-2H-pyran-2-yl)oxy]decyl]-2H-tetrazol-5-yl]urea was substituted for N-[2,6-bis-(1-methylethyl)-phenyl]-N'-[2-[(tetrahydro-2H-pyran-2-yl) oxy]dodecyl]-2H-tetrazol-5-yl]urea and the general procedure of Example 1(d) was followed the following respective products were obtained:

EXAMPLE 14

N-[2,6-Bis(1-methylethyl)phenyl]-N'-[2-(11-hydroxyundecyl) -2H-tetrazol-5-yl]urea, m.p. 84–87° C.

EXAMPLE 15

N-[2,6-Bis(1-methylethyl)phenyl]-N'-[2-(10-hydroxydecyl)-2H-tetrazol-5-yl]urea, m.p. 102–107° C.

EXAMPLE 16

N-(2,6-Dimethylphenyl)-N'-(1-phenylmethyl-1H-tetrazol-5-yl)urea (a) Following the general procedure of Example 2 only substituting an appropriate amount of benzyl chloride for 1-bromodecane, 5-amino-2-benzyltetrazole and 5-amino-1-benzyltetrazole were obtained.

(b) 5-Amino-1-benzyltetrazole (3.25 g, 0.0186 mol) was suspended in 15 mL of 1,2-dichloroethane after which 2,6-dimethylphenylisocyanate (3.5 mL, 0.025 mol) was added. The mixture was refluxed for 6 hours, 10 mL of dimethylformamide was added, and the mixture was refluxed for an additional 6 hours. The reaction mixture was diluted twice with 50 mL water and the water decanted from the precipitate then concentrated in vacuo adding ethanol as the azeotropic solvent. The precipitate was washed with ether, dried in a vacuum oven, washed with hot water and hot ethyl acetate, extracted with hot 9:1 methanol/methylene chloride, and concentrated to give the title compound, m.p. 220–230° C. dec.

When in the above procedure 5-amino-2-decyltetrazole is substituted for 1-benzyltetrazole N-(2,6-dimethylphenyl)-N'-(2-decyl-2H-tetrazol-5-yl)-urea is obtained.

EXAMPLE 17

N-[2,6-Bis(1-methylethyl)phenyl]-N'-(2-phenylmethyl-2H-tetrazol-5-yl)urea

5-Amino-2-benzyltetrazole (1.55 g, 8.84 mmol) was dissolved in 20 mL methylene chloride after which 2,6-diisopropylphenyl isocyanate (2.25 mL, 10.6 mmol) and 1.5 mL triethylamine was added. The mixture was stirred at room temperature for 4 days then quenched with 5 mL 2N sulfuric acid and extracted with 50 mL ethyl acetate. The organic layer was washed with water and a saturated aqueous solution of sodium carbonate, dried over magnesium sulfate, filtered, and evaporated, leaving a white solid which was recrystallized from ethyl acetate/ether to give the title compound, m.p. 180–181° C.

EXAMPLE 18

N-(2,6-Dimethylphenyl)-N'-(2-phenylmethyl-2H-tetrazol-5-yl)urea

Following the general procedure of Example 17, only substituting an appropriate amount of 2,6-dimethylphenyl isocyanate for 2,6-diisopropylphenyl isocyanate, the title compound was obtained, m.p. 230–235° C (dec).

EXAMPLE 19

N-[2,6-Bis(1-methylethyl)phenyl]-N'-(1-phenylmethyl-1H-tetrazol-5-yl)urea

Following the general procedure of Example 17, only substituting an appropriate amount of 5-amino-1-benzyltetrazole for 5-amino-2-benzyltetrazole, the title compound was obtained, m.p. 195–197° C.

EXAMPLE 20

N-2,6-Bis(1-methylethyl)phenyl]-N'-(1-decyl-1H-tetrazol-5-yl)urea

5-Amino-1-decyltetrazole (3.50 g, 0.0155 mol) and 2,6-diisopropylphenyl isocyanate (3.65 mL, 0.017 mol) were dissolved in 100 mL 1,2-dichloroethane to which 2.4 mL of triethylamine was added. The reaction mixture was heated to reflux for 8 hours, stirred overnight, then partitioned between saturated aqueous ammonium chloride and methylene chloride. The organic layer was washed twice with water, then dried over magnesium sulfate, filtered and evaporated, leaving a solid. The solid was flash chromatographed on silica gel in ethyl acetate/hexane to give the title compound which was recrystallized from hexane at −78° C, yielding white crystals, m.p. 135–136° C.

EXAMPLE 21

N-2,6-Bis(1-methylethyl)phenyl]-N'-(1-phenylethyl-1H-tetrazol-5-yl)urea

5-Amino-1-phenylethyltetrazole (3.87 g) was dissolved in 150 m of 1:1 methylene chloride/tetrahydrofuran and 2.5 mL of triethylamine and 2,6-diisopropylphenyl isocyanate (4.5 mL) were added. The mixture was stirred for 72 hours at room temperature and 5 hours at 50° C, then partitioned between saturated ammonium chloride and ethyl acetate. The organic layer was washed with water, dried over magnesium sulfate, filtered, and evaporated. The resulting solid was recrystallized from diethylether/hexane to give the title compound, yield 2.14 g.

EXAMPLE 22

N-[2,6-Bis(1-methylethyl)phenyl]-N'-(2-octyl-2H-tetrazol-5-yl)urea

A mixture of N-[2,6-bis(1-methylethyl)phenyl]-N'-(1H'-tetrazol-5-yl)urea (2.0 g, 6.94 mmol), 1-bromooctane (1.8 mL, 10.4 mmol) and triethylamine (1.0 mL, 7 mmol) in a 1:1 mixture of dimethyl-formamide/toluene (100 mL) was heated to reflux for 18 hours, then cooled and partitioned between 1N hydrochloric acid and ethyl acetate. The organic layer was washed extensively with water, dried over magnesium sulfate, filtered and the filtrate evaporated to dryness. The remaining solid was flash chromatographed on silica gel in ethyl acetate/hexane to give the title compound, m.p. 139–140° C.

EXAMPLE 23

N-[2,6-Bis(1-methylethyl)phenyl]-N'-(2-hexyl-2H-tetrazol-5-yl)urea

When in the general procedure of Example 22 an appropriate amount of 1-bromohexane is substituted for 1-bromooctane, the title compound was obtained, m.p. 154–156° C.

EXAMPLE 24

N-[2,6-Bis(1-methylethyl)phenyl]-N'-(2-decyl-2H-tetrazol-5-yl)urea

When in the general procedure of Example 21 an appropriate amount of 5-amino-2-decyltetrazole is substituted for 5-amino-1-phenylethyltetrazole, the title compound was obtained, yield 2.8 g.

EXAMPLE 25

Following the general procedure of Example 2(a), only substituted for 1-bromododecane an appropriate amount of 1-bromodecane, 2-phenethylbromide, 1-bromohexane, 1-bromooctane, or 1-bromododecane, the following respective products were obtained:
5-amino-1-decyltetrazole,
5-amino-2-decyltetrazole,
5-amino-1-phenethyltetrazole,
5-amino-2-phenethyltetrazole,
5-amino-1-hexyltetrazole,
5-amino-2-hexyltetrazole,
5-amino-1-octyltetrazole,
5-amino-2-octyltetrazole,
5-amino-1-dodecyltetrazole, and
5-amino-2-dodecyltetrazole.

CHART I

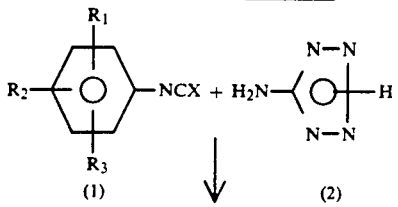

CHART I -continued

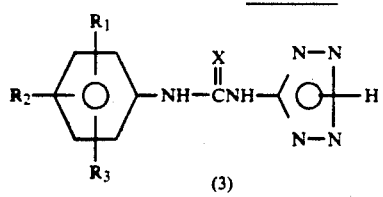

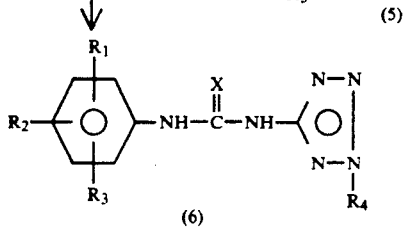

CHART II

We claim:
1. A compound of the formula wherein X is oxygen or sulfur; wherein each of $R_1$, $R_2$, and $R_3$ is the same or different and is selected from
hydrogen;
fluorine;
chlorine;
bromine;
a straight or branched alkyl group having from one to six carbon atoms;
a straight or branched alkoxy group having from one to six carbon atoms;
benzoyl which is unsubstituted or is substituted on the aromatic ring with from one to three substituents selected from fluorine, chlorine, bromine, iodine, a straight or branched alkyl group having from one to six carbon atoms or a straight or branched alkoxy group having from one to six carbon atoms;
benzyl which is unsubstituted or is substituted on the aromatic ring with from one to three substituents selected from fluorine, chlorine, bromine, iodine, a straight or branched alkyl group having from one to six carbon atoms or a straight or branched alkoxy group having from one to six carbon atoms;
phenyl which is unsubstituted or is substituted with from one to three substituents selected from fluorine, chlorine, bromine, iodine, a straight or branched alkyl group having from one to six carbon atoms, or a straight or branched alkoxy group having from one to six carbon atoms;
$NR_5R_6$ wherein each of $R_5$ and $R_6$ is the same or different and is hydrogen, a straight or branched alkyl group having from one to four carbon atoms or —$NR_5R_6$ taken together form monocyclic heterocyclic group selected from pyrrolidino, piperidino, piperazino or piperazino substituted on the 4-position with a straight or branched alkyl group having from one to four carbon atoms;
—$COR_7$ wherein $R_7$ is hydroxy, a straight or branched alkoxy group having from one to six carbon atoms, benzyloxy which is unsubstituted or is substituted on the aromatic ring with from one to three substituents selected from fluorine, chlorine, bromine, iodine, a straight or branched alkyl group having from one to six carbon atoms or a straight or branched alkoxy group having from one to six carbon atoms, or $R_7$ is —$NR_5R_6$ wherein $R_5$ and $R_6$ have the meanings defined above;
wherein $R_4$ is attached to either the 1- or 2-position of the tetrazole ring and is selected from
(a) a straight or branched hydrocarbon chain having from one to twenty carbon atoms and which is saturated or contains from one to three double bonds and wherein said chain is unsubstituted or is substituted with one or two substituents selected from fluorine, chlorine, bromine, iodine, straight or branched alkoxy having from one to four carbon atoms, hydroxy, or tetrahydro-pyran-6-yloxy;
(b) a spiroalkyl group of the formula $$-CH_2)_m-C-(CH_2)_n-CH_3$$
$$(CH_2)_p$$

wherein each of m and n is independently zero or one to six, and p is two to six;
(c) the group -$(CH_2)_qNR_8R_9$ wherein q is two to four and each of $R_8$ and $R_9$ is hydrogen or a straight or branched alkyl group having from one to 20 carbon atoms provided that one of $R_8$ and $R_9$ is other than hydrogen; or (d) the group $-(CH_2)_r$-phenyl wherein r is zero to four and the phenyl moiety is unsubstituted or substituted with from one to three substituents selected from fluorine, chlorine, bromine, iodine, a straight or branched alkyl group having from one to six carbon atoms, or a straight or branched alkoxy group having from one to six carbon atoms; and pharmaceutically acceptable salts thereof with the proviso that when $R_4$ is phenyl on the 1-position of the tetrazole ring at least one of $R_1$, $RH_2$, and $R_3$ is other than hydrogen.

2. A compound of claim 1 wherein X is oxygen.

3. A compound of claim 2 wherein $R_4$ is on the 2-position of the tetrazole ring.

4. A compound of claim 3 wherein $R_1$, $R_2$, and $R_3$ are in 2, 4, and 6-positions of the phenyl ring to which they are attached.

5. A compound of claim 4 wherein each of $R_1$, $R_2$, and $R_3$ is methoxy.

6. A compound of claim 4 wherein each of $R_1$, $R_2$, and $R_3$ is fluoro.

7. A compound of claim 3 wherein $R_4$ is a straight or branched hydrocarbon chain having from one to 20 carbon atoms and which is saturated or contains from one to three double bonds and wherein said chain is unsubstituted or substituted with one or two substituents selected from fluorine, chlorine, bromine, iodine, straight or branched alkoxy having from one to four carbon atoms, hydroxy or tetrahydropyran-6-yloxy.

8. A compound of claim 7 wherein $R_2$ is hydrogen, $R_1$ is on the 2-position of the phenyl ring to which it is attached, and Ra is on the 6-position of the phenyl ring which it is attached.

9. A compound of claim 8 wherein $R_2$ and $R_3$ are straight or branched alkyl having from one to six carbon atoms.

10. A compound of claim 9 wherein $R_2$ and $R_3$ are 1-methylethyl.

11. A compound of claim 10 which is

N-[2,6-bis(1-methylethyl)phenyl]-N'-(2-tetra-decyl-2H-tetrazol-5-yl)urea,

N-[2,6-bis(1-methylethyl)phenyl]-N'-(2-tridecyl-2H-tetrazol-5-yl)urea,

N-[2,6-bis(1-methylethyl)phenyl]-N'-(2-dodecyl-2H-tetrazol-5-yl)urea,

N-[2,6-bis(1-methylethyl)phenyl]-N'-(2-hexadecyl-2H-tetrazol-5-yl)urea,

N-[2,6-bis(1-methylethyl)phenyl]-N'-(2-nonyl-2H-tetrazol-5-yl)urea,

N-[2,6-bis(1-methylethyl)phenyl]-N'-(2-undecyl-2H-tetrazol-5-yl)urea,

N-[2,6-bis(1-methylethyl)phenyl]-N'-(2-butyl-2H-tetrazol-5-yl)urea,

N-[2,6-bis(1-methylethyl)phenyl]-N'-[2-(10methoxycarbonyldecyl)-2H-tetrazol-5-yl]urea, N-[2,6-bis(1-methylethyl)phenyl]-N'-(2-octyl-2H-tetrazol-5-yl)urea, N-[2,6-bis(1-methylethyl)phenyl]-N'-(2-hexyl-2H-tetrazol-5-yl)urea, N-[2,6-bis(1-methylethyl)phenyl]-N'-(2-decyl-2H-tetrazol-5-yl)urea, N-[2,6-bis(1-methylethyl)phenyl]-N'-[2-[[tetra-hydro-2H-pyran-2-yl)oxy]dodecyl]-2H-tetrazol-5-yl]urea, N-[2,6-bis(1-methylethyl)phenyl]-N'-[2-(12-hydroxydodecyl)-2H-tetrazol-5-yl]urea, N-[2,6-bis(1-methylethyl)phenyl]-N'-[2-[(tetra-hydro-2H-pyran-2-yl)oxy]decyl-2H-tetrazol-5-yl]-urea, N-[2,6-bis(1-methylethyl)phenyl]-N'-[2-[(tetra-hydro-2H-pyran-2-yl)oxy]undecyl-2H-tetrazol-5-yl]-urea, N-[2,6-bis(1-methylethyl)phenyl]-N'-[2-(3,7-dimethyl-2,6-octadienyl)-2H-tetrazol-5-yl]urea, N-[2,6-bis(1-methylethyl)phenyl]-N'-[2-(11-hydroxyundecyl)-2H-tetrazol-5-yl]urea,or N-[2, 6-bis(1-methylethyl)phenyl]-N'-[2-(10-hydroxydecyl)-2H-tetrazol-5-yl]urea.

12. A compound of claim 3 wherein $R_4$ is the group $-(CH_2)_r$-phenyl wherein r is zero to four and the phenyl moiety is unsubstituted or substituted with from one to three substituents selected from fluorine, chlorine, bromine, iodine, a straight or branched alkyl group having from one to six carbon atoms, or a straight or branched alkoxy group having from one to six carbon atoms.

13. A compound of claim 12 wherein $R_2$ is hydrogen, $R_1$ is on the 2-position of the phenyl ring to which it is attached, and $R_3$ is on the 6-position of the phenyl ring to which it is attached.

14. A compound of claim 13 wherein $R_2$ and $R_3$ are straight or branched alkyl having from one to six carbon atoms.

15. A compound of claim 14 wherein $R_2$ and $R_3$ are 1-methylethyl.

16. A compound of claim 15 which is N-[2,6-bis(1-methylethyl) phenyl]-N'-(2-(phenylmethyl-2H-tetrazol-5-yl)urea.

17. A compound of claim 2 wherein $R_4$ is on the position of the tetrazole ring.

18. A compound of claim 17 which is

N-[2,6-bis(1-methylethyl) phenyl]-N'-[1-dodecyl-1H-tetrazol-5-yl]urea,

N-(2,6-dimethylphenyl)-N'-(1-phenylmethyl-1tetrazol-5-yl)urea,

N-[2,6-bis ('-methylethyl)phenyl]-N'-(1-phenyl-methyl-1H-aetrazol-5-yl)urea, or

N-[2,6-bis(1-methylethyl)phenyl]-N'-(1-phenyl-ethyl-1H-tetrazol-5-yl)urea.

19. A pharmaceutical composition comprising a compound of claim 1 and a pharmaceutically acceptable carrier.

20. A method of treating atherosclerosis in a patient in need of treatment which comprises administering to said patient an effective amount of a compound of claim 1.

* * * * *